United States Patent
Tidare et al.

(10) Patent No.: US 7,219,528 B2
(45) Date of Patent: May 22, 2007

(54) SAMPLE FLOW POSITIONING METHOD AND ANALYTICAL SYSTEM USING THE METHOD

(75) Inventors: Mattias Tidare, Uppsala (SE); Roos Håkan, Uppsala (SE)

(73) Assignee: Biacore AB, Uppsala (SE)

( * ) Notice: Subject to any disclaimer, the term of this patent is extended or adjusted under 35 U.S.C. 154(b) by 242 days.

(21) Appl. No.: 11/005,492

(22) Filed: Dec. 6, 2004

(65) Prior Publication Data

US 2005/0199076 A1    Sep. 15, 2005

Related U.S. Application Data

(60) Provisional application No. 60/528,950, filed on Dec. 10, 2003.

(30) Foreign Application Priority Data

Dec. 10, 2003    (SE) .................................... 0303319

(51) Int. Cl.
*G01N 21/00*    (2006.01)
(52) U.S. Cl. ....................... 73/1.02; 436/174
(58) Field of Classification Search ..................... None
See application file for complete search history.

(56) References Cited

U.S. PATENT DOCUMENTS

| | | | |
|---|---|---|---|
| 5,972,710 A | 10/1999 | Weigl et al. | 436/34 |
| 2001/0055817 A1 | 12/2001 | Malmqvist et al. | 436/531 |

FOREIGN PATENT DOCUMENTS

| | | |
|---|---|---|
| EP | 0 288 029 A2 | 10/1988 |
| WO | WO 99/36766 | 7/1999 |
| WO | WO 00/56444 | 9/2000 |

*Primary Examiner*—Robert Raevis
(74) *Attorney, Agent, or Firm*—Seed IP Law Group PLLC (57) ABSTRACT

A method of positioning a laminar flow of a sample fluid on a surface within a flow cell is disclosed. The method comprises providing a laminar flow of a first guiding fluid adjacent to a laminar flow of a second guiding fluid different from the first guiding fluid such that the two fluids flow together over the surface with a detectable interface to each other; detecting the interface between the two different guiding fluids; optionally adjusting the interface laterally to a desired position by adjusting the relative flow rates of the two guiding fluids; and introducing a laminar flow of the sample fluid between the laminar flows of the first and second guiding fluids such that the flow of the sample fluid is sandwiched between the guiding fluids. An analytical system for carrying out the method, a computer program, a computer program product and a computer system for performing the method are also disclosed.

24 Claims, 6 Drawing Sheets

PRIOR ART

FIGURE 1

PRIOR ART

| Time | (All) |
|---|---|
| Cycle | (All) |
| Window | (All) |

| Average of RelResp | | DiodeRow | | | | | | | | | | |
|---|---|---|---|---|---|---|---|---|---|---|---|---|
| APROG | Id | 17 | 18 | 19 | 20 | 21 | 22 | 23 | 24 | 25 | 26 | 27 |
| test_puls9_FLOW_GRADIENT | 2 | 1,00 | 0,94 | 0,16 | 0,01 | 0,01 | 0,01 | 0,00 | 0,00 | 0,00 | 0,01 | 0,00 |
| | 4 | 1,00 | 0,99 | 0,34 | 0,01 | 0,01 | 0,01 | 0,00 | 0,00 | 0,00 | 0,01 | 0,00 |
| | 6 | 0,93 | 1,00 | 0,54 | 0,02 | 0,01 | 0,01 | 0,00 | 0,00 | 0,00 | 0,01 | 0,00 |
| | 8 | 0,73 | 1,00 | 0,72 | 0,04 | 0,01 | 0,01 | 0,00 | 0,00 | 0,00 | 0,00 | 0,00 |
| | 10 | 0,47 | 1,01 | 0,86 | 0,08 | 0,01 | 0,01 | 0,00 | 0,00 | 0,00 | 0,00 | 0,00 |
| | 12 | 0,23 | 1,00 | 0,96 | 0,16 | 0,01 | 0,01 | 0,00 | 0,00 | 0,00 | 0,00 | 0,00 |
| | 14 | 0,07 | 0,97 | 0,99 | 0,31 | 0,01 | 0,01 | 0,00 | 0,00 | 0,00 | 0,00 | 0,00 |
| | 16 | 0,01 | 0,83 | 1,00 | 0,50 | 0,01 | 0,01 | 0,00 | 0,00 | 0,00 | 0,00 | 0,00 |
| | 18 | 0,01 | 0,62 | 1,00 | 0,67 | 0,02 | 0,01 | 0,00 | 0,00 | 0,00 | 0,00 | 0,00 |
| | 20 | 0,01 | 0,40 | 1,00 | 0,82 | 0,05 | 0,01 | 0,00 | 0,00 | 0,00 | 0,00 | 0,00 |
| | 22 | 0,00 | 0,20 | 1,00 | 0,92 | 0,12 | 0,01 | 0,00 | 0,00 | 0,00 | 0,00 | 0,00 |
| | 24 | 0,00 | 0,07 | 0,95 | 0,99 | 0,23 | 0,01 | 0,00 | 0,00 | 0,00 | 0,00 | 0,00 |
| | 26 | 0,00 | 0,02 | 0,82 | 1,00 | 0,38 | 0,01 | 0,00 | 0,00 | 0,00 | 0,00 | 0,00 |

SAMPLE FLOW POSITIONING METHOD AND ANALYTICAL SYSTEM USING THE METHOD

BACKGROUND OF THE INVENTION

1. Field of the Invention

The present invention relates to sheath flow techniques, and more particularly to a method of positioning a laminar flow of a sample fluid on a surface within a flow cell by guiding the sample fluid flow between two laminar flows of guiding fluids. The invention also relates to an analytical system, a computer program product and a computer system for performing the method.

2. Description of the Related Art

WO 99/36766 discloses methods for selectively contacting defined lanes or strips of a surface within a flow cell with a fluid capable of interacting therewith, such as a sensitizing fluid or a sample fluid, using a laminar flow technique usually referred to as hydrodynamic addressing. In one embodiment, the laminar flow of the sensitizing (or sample) fluid is guided between two buffer flows and may be positioned as desired over the surface by adjusting the relative flow rates of the buffer flows. This may be accomplished in a flow cell of the type having three inlets and one outlet (a so-called Ψ- or psi-cell), the interacting fluid being introduced through the central inlet and the guiding buffer fluids through the other two inlets.

Methods for detecting interactions of a fluid with the flow cell surface in WO 99/36766 include surface plasmon resonance (SPR) spectroscopy which measures refractive index changes at the surface caused by the interactions. Since the SPR detection response is influenced by the refractive index of the fluid medium in the vicinity of the surface, SPR detection may also be used to detect the position of a sensitizing or sample fluid flow on the surface when calibrating the flow cell with respect to interface position and flow rates. This may be done by replacing the interacting fluid by a fluid having approximately the same viscosity but which does not interact with the surface and which has a different refractive index than the buffer. Thereby each interface between the sample fluid and the two buffer flows can be detected. When the flow cell has been calibrated, each lateral position of the interacting fluid flow corresponds to a defined setting of the relative flow rates of the buffer flows.

WO 00/56444 discloses a similar use of a Ψ-cell as the above-mentioned WO 99/36766. In one embodiment, parallel multiple sample streams, separated by guiding streams, are passed through a flow channel. To position the sample streams, two main guidance streams are first introduced, and their flow rates are adjusted to produce an interface at a desired lateral position. The flows of the sample streams and their guiding streams are then introduced between the two main guidance streams.

It is an object of the present invention to provide an improved method of positioning the central fluid flow in a flow cell of the Ψ-cell type.

BRIEF SUMMARY OF THE INVENTION

According to the present invention, the above and other advantages are provided by using two different guiding fluids to position a flow of surface-interacting fluid, below referred to as sample fluid, or simply sample. Provided that the two guiding fluids differ sufficiently from each other in at least one detectable property, e.g., refractive index in the case of SPR detection, the interface between the two fluids may be detected and positioned as desired. The position of this interface will then determine the position of the sample flow when introduced between the two guiding fluids. In this way, no other fluid than the two guiding fluids will be required to set or calibrate the positioning of the sample fluid.

In one aspect, the present invention therefore provides a method of positioning a laminar flow of a sample fluid on a surface within a flow cell, which method comprises the steps of:

a) providing a laminar flow of a first guiding fluid adjacent to a laminar flow of a second guiding fluid different from the first guiding fluid such that the two fluids flow together over the surface with a detectable interface to each other, b) detecting the interface between the two different guiding fluids, c) optionally, adjusting the interface laterally to a desired position by adjusting the relative flow rates of the two guiding fluids, and d) introducing a laminar flow of the sample fluid between the laminar flows of the first and second guiding fluids such that the flow of the sample fluid is sandwiched between the guiding fluids.

In another aspect, the present invention provides a method of positioning a laminar flow of a sample fluid on a surface within a flow cell, which method comprises:

A. a calibration procedure which comprises the steps of:
  a) providing a laminar flow of a first guiding fluid adjacent to a laminar flow of a second guiding fluid different from the first guiding fluid such that the two fluids flow together over the surface with a detectable interface to each other,
  b) detecting the interface between the two different guiding fluids,
  c) optionally, adjusting the interface laterally to a defined position by adjusting the relative flow rates of the two guiding fluids,
  d) storing flow rate-related settings corresponding to the position of the interface, and
  e) optionally, repeating steps c) and d) to obtain flow rate-related settings for at least two different defined positions of the interface; and B. a sample introduction procedure which comprises the steps of:
  f) applying calibrated flow rate-related settings to two guiding fluids (preferably the first and second guiding fluids used in procedure A) to obtain laminar flows thereof with the interface at a defined position,
  g) introducing a laminar flow of the sample fluid between laminar flows of the two guiding fluids such that the flow of the sample fluid is sandwiched between the guiding fluids, and
  h) optionally repeating steps f) and g) at least once with the interface at a different defined position.

In still another aspect, the present invention provides an analytical system which comprises data processing means for performing at least one of the above methods.

In still another aspect, the present invention provides a computer program comprising program code means for performing at least one of the above methods.

In yet another aspect, the present invention provides a computer program product comprising program code means stored on a computer readable medium or carried on an electrical or optical signal for performing at least one of the above the methods.

In still another aspect, the present invention provides a computer system containing a computer program comprising program code means for performing at least one of the above methods.

Other advantages, novel features and objects of the invention will become apparent from the following description of the invention when considered in conjunction with the accompanying drawings.

DETAILED DESCRIPTION OF THE INVENTION

As mentioned above, this invention is generally directed to the positioning of a laminar flow of a sample fluid on a surface within a flow cell of the ψ-type, i.e., where a laminar flow of a sample fluid is guided between two laminar flows of guiding fluid. The surface is usually a sensing surface. This term as used herein generally relates to a solid support surface where binding or adsorption events may be detected, e.g., by optical means. An exemplary sensing surface is a biosensor surface. (A biosensor is usually defined as a device using a component for molecular recognition, e.g., a layer or pattern with immobilized antibodies, in either direct conjunction with a solid state physicochemical transducer, or with a mobile carrier bead/particle being in conjunction with the transducer.) Other examples are DNA or protein chips.

Figure 1:
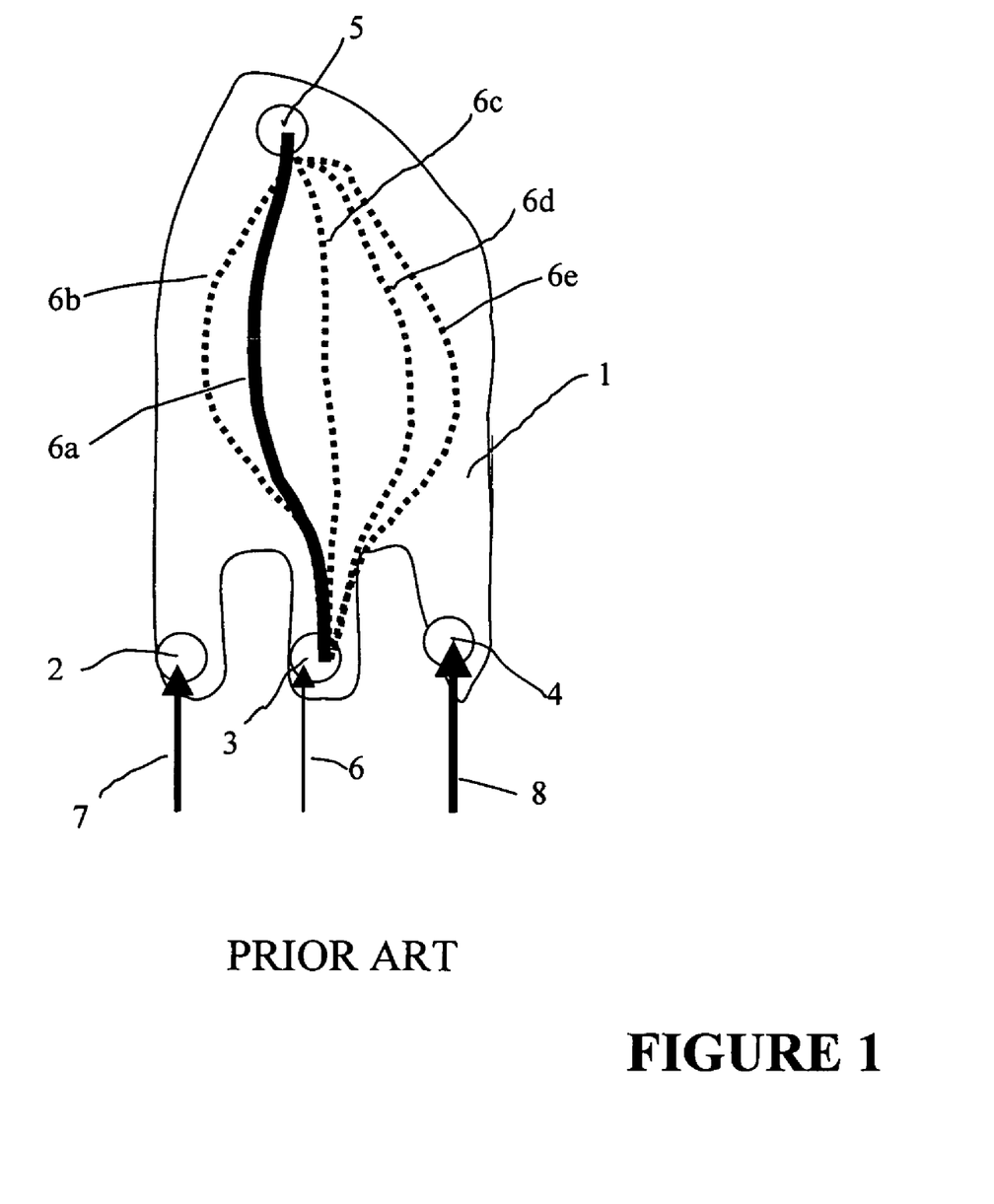
FIG. 1 is a schematic illustration of a ψ-flow cell.

An example of a ψ-type flow cell is schematically shown in FIG. 1. The flow cell has a flow chamber, or flow channel, 1 having an inlet end with three inlet ports 2, 3 and 4, and an outlet end with a single outlet port 5. A laminar flow 6 of sample fluid (e.g., containing a ligand to be immobilized on the sensing surface) is introduced through the central inlet port 3 by means of a pump (not shown). Laminar flows 7 and 8 of guiding fluid, such as buffer, are introduced through inlet ports 2 and 4, respectively, by respective pumps (not shown). The three laminar flows will flow together through the flow channel 1 with the sample flow 6 sandwiched between the two flows of guiding fluid, exiting through outlet port 5. While the width of the sample fluid flow path 6a (solid line) is determined by the relative flow rate of the sample fluid flow in relation to the flow rates of the two guiding fluid flows (and also by the viscosity of the sample fluid), the lateral position of the sample fluid flow path in the flow cell is determined by the relative flow rates of the two flows of guiding fluid. Thus, by adjustment of the flow rate ratio of the guiding fluid flows, the sample flow may be laterally positioned as desired in the flow cell, as indicated by the dashed sample fluid paths 6b to 6e in the Figure. In this way, the sample fluid flow may be made to selectively contact a desired area of the flow cell, a technique usually referred to as hydrodynamic addressing. This may, for instance, be used to immobilize ligands at defined lanes or areas on a sensing surface, or to selectively contact a defined lane or area on the sensing surface with a sample fluid containing ligand-binding analyte, as described in, for example, the aforementioned WO 99/36766 and WO 00/56444 (the entire disclosures of which are incorporated by reference herein).

Various detection techniques may be used to detect the binding interactions of ligand or analyte, respectively, at the sensing surface, label-free techniques as well as techniques requiring a label or tag. A typical label-free technique for which there are commercially available detection systems is surface plasmon resonance (SPR) spectroscopy.

The phenomenon of SPR is well known, suffice it to say that SPR arises when light is reflected under certain conditions at the interface between two media of different refractive indices, and the interface is coated by a metal film, typically silver or gold. SPR causes a reduction in the intensity of the reflected light at a specific angle of reflection. This angle of minimum reflected light intensity varies with the refractive index close to the surface on the side opposite from the reflected light.

Figure 2:
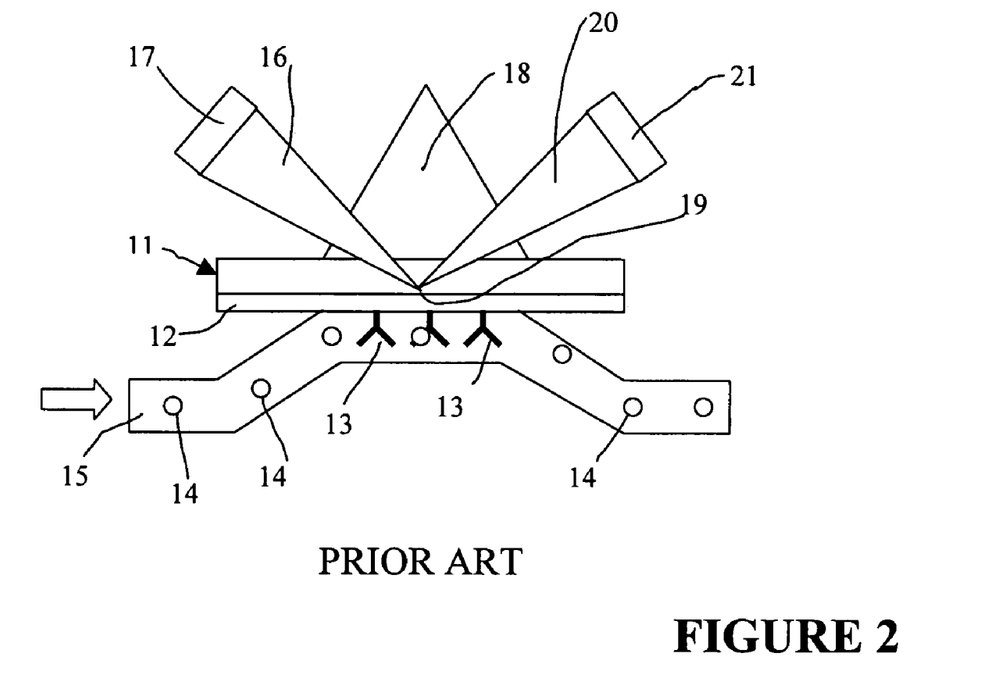
FIG. 2 is a schematic side view of a biosensor system based on SPR.

A schematic illustration of an exemplary SPR sensor system is shown in FIG. 2. Sensor chip 11 has a gold film 12 supporting capturing molecules 13, e.g., antibodies, exposed to a sample flow with analytes 14, e.g., an antigen, through a flow channel 15. Monochromatic p-polarised light 16 from a light source 17 is coupled by a prism 18 to the glass/metal interface 19 where the light is totally reflected. The intensity of the reflected light beam 20 is detected by an optical detection unit 21, typically a photodetector array.

When molecules in the sample bind to the capturing molecules on the sensor chip surface, the concentration, and therefore the refractive index at the surface, changes and an SPR response is detected. Plotting the response against time during the course of an interaction will provide a quantitative measure of the progress of the interaction. With reference to the flow cell in FIG. 1, the lateral positions in the flow cell correspond to different rows in the detector array upon which the respective surface positions, or areas, are imaged.

It is readily seen that correct guidance of a sample flow over the sensing surface is important. It is therefore usually necessary to perform some kind of calibration to be able to determine in advance where the sample flow path will be positioned laterally for different settings of the relative flow rates. Typically, such calibration may be performed using, instead of the sample fluid, a test fluid which is different from the guiding fluid and which does not react with the sensing surface. Detection of the lateral position of the test fluid may be based on a detectable difference between the test fluid and the guiding fluid, e.g., refractive index for an SPR based detection system.

According to the present invention, it has now been found that correct positioning of the sample flow position may be conveniently performed without the use of a test fluid. Thus, by using two different guiding fluids for the guiding fluid flows (rather than a single fluid for both guiding fluid flows), which guiding fluids differ in at least one detectable property, the positioning may be made with the guiding fluid flows alone (usually buffer fluids), i.e., in the absence of test or sample fluid, by monitoring and positioning the interface between the two different guiding fluids.

In one embodiment, once the interface has been correctly positioned, the sample fluid flow is introduced between the flows of the two guiding fluids, causing the centre of the sample fluid to take this position. The width of the sample fluid flow may then be adjusted by following the respective interfaces between the sample fluid and the guiding fluids, as will be described in more detail below.

In another alternative embodiment, following and positioning the interface between the two different guiding fluids as above may be used to precalibrate the flow cell with respect to the guiding fluid flow rate-related data (usually pump settings) that correspond to various positions of the sample fluid flow. To introduce a sample flow at a desired lateral position in the flow cell, the necessary flow rates of the guiding fluids are then set, whereupon the sample flow is introduced. While it is preferred to use the same guiding fluids as those used for the calibration also when introducing the sample flow, it is (at least in theory) possible to use other guiding fluids, or the same guiding fluid on both sides of the sample flow (e.g., one of the guiding fluids used in the calibration).

While refractive index, as mentioned above, may be used as a detectable property of the guiding fluids, other detectable properties for the purposes of the invention include absorbancy and light emission, just to mention a few. The necessary difference in the detectable property between the two guiding fluids depends on the detectable property and the detection system used and may readily be determined by a person skilled in the art.

Usually (but not necessarily), the same detection technique as that used for detecting molecular interaction changes at the sensing surface(s) is also used for detecting the position of the interface between the guiding fluids. Typical such detection techniques are sensor-based and include, but are not limited to, mass detection methods, such as optical, thermo-optical, piezoelectric or acoustic wave methods, including, e.g., surface acoustic wave (SAW) and quartz crystal microbalance (QCM) methods, and electrochemical methods, such as potentiometric, conductometric, amperometric and capacitance/impedance methods. With regard to optical detection methods, representative methods include those that detect mass surface concentration, such as reflection-optical methods, including both external and internal reflection methods, angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors, external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Biosensor systems based on SPR are commercially available today. Exemplary such SPR-biosensors include the BIACORE® instruments sold by Biacore AB (Uppsala, Sweden). A detailed discussion of the technical aspects of the BIACORE® instruments and the phenomenon of SPR may be found in U.S. Pat. No. 5,313,264 (the full disclosure of which is incorporated by reference herein). In the BIACORE® system, the SPR response values are expressed in resonance units (RU). One RU represents a change of 0.0001° in the angle of minimum reflected light intensity.

For an SPR based sensor system like the BIACORE® system, a difference in refractive index between the two guiding fluids of, say, about 100 RU may be convenient, and the fluid interface position may be determined by means of per se conventional sensorgrams. With reference to FIG. 1 again, assume that the detector of the detecting system is a photodetector array and that the width of each sample flow path, as represented by flow paths 6a–6e in the Figure, is selected to cover a detector row in the array when imaged thereon. A positioning of the interface in the middle of a detector row will result in averaging of the refractive indices from the two guiding fluids, giving a response of 50 RU (for a refractive index difference of 100 RU between the guiding fluids).

Figure 3:
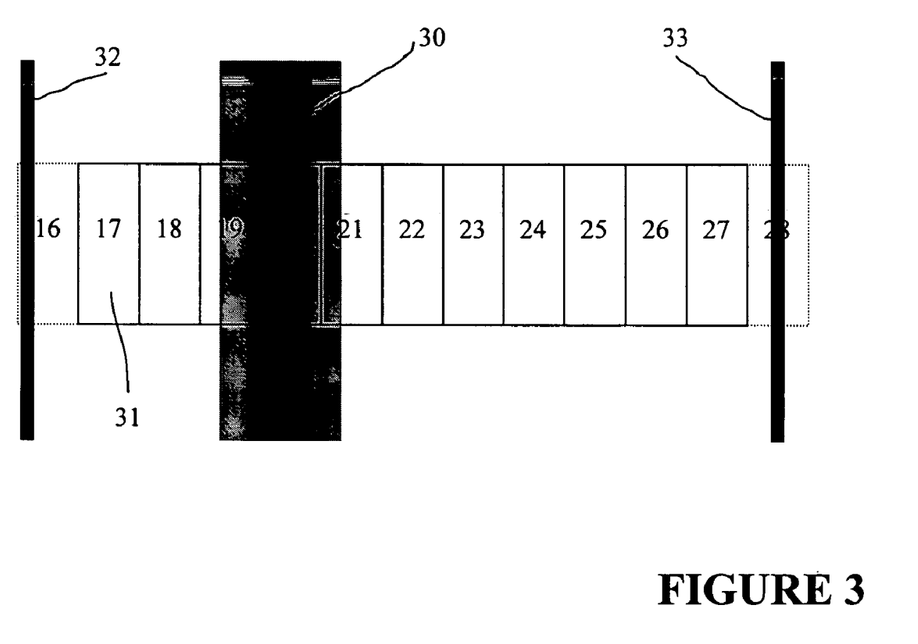
FIG. 3 is a schematic illustration of a portion of a flow cell where the areas imaged on an array detector and a sample flow are shown.

FIG. 3 is a schematic illustration showing a surface portion of a ψ-flow cell with a sample flow streak 30 guided between two flows of guiding fluid (not shown). The numbered squares 31 indicate individual photodetector rows of an SPR detector array upon which the respective surface areas are imaged. Reference numerals 32 and 33 designate the walls of the ψ-flow cell. In the Figure, the sample flow 30 covers detector row 21 and about half of the detector rows 20 and 22, respectively. In order to, for example, enable immobilization of as many streaks of ligands as possible in the flow cell, the sample flow should, of course, have been placed over a single detector row. It is preferred that the design of the flow cell and pump system for supplying the guiding fluids permits an accuracy in setting the interface of about 10 μm or better.

After the interface between the two different guiding fluids has been set at a desired position (i.e., detector row in FIG. 3), the sample fluid flow is introduced into the flow cell, where it will be pressed in between the guiding fluids and centred over the previous interface between the guiding fluids. The width of the sample fluid flow is determined by the relative flow rate of the sample fluid flow and the viscosity of the sample fluid. Since the viscosity of the sample fluid is not always known, the flow rate of the sample fluid flow may have to be adjusted until the desired width is obtained. When a detector array is used for the detection as in the embodiment shown in FIG. 3, the width of the sample fluid may be followed by measuring the noise of neighbouring detectors. Such a noise is likely to be present to a higher or lower degree depending on the stability of the sample/guiding fluid interfaces. Thus, as soon as the interface between the sample fluid flow and a guiding fluid just touches a detector row, the noise will increase.

It may be preferred to keep the total flow rate constant when introducing the sample flow. In such a case the flow rates of the two guiding fluids are reduced while maintaining the flow rate ratio between them. Assume, for example, that the flow rate of one guiding fluid is 70 μl/min and the flow rate of the other guiding fluid is 30 μl/min, the total flow rate being 100 μl/min, and that a sample fluid flow of 20 μl/min is introduced between the guiding fluids. To maintain the total fluid flow rate at 100 μl/min, the flow rates of the guiding fluids will have to be reduced to 60 and 20 μl/min, respectively.

Figure 4:
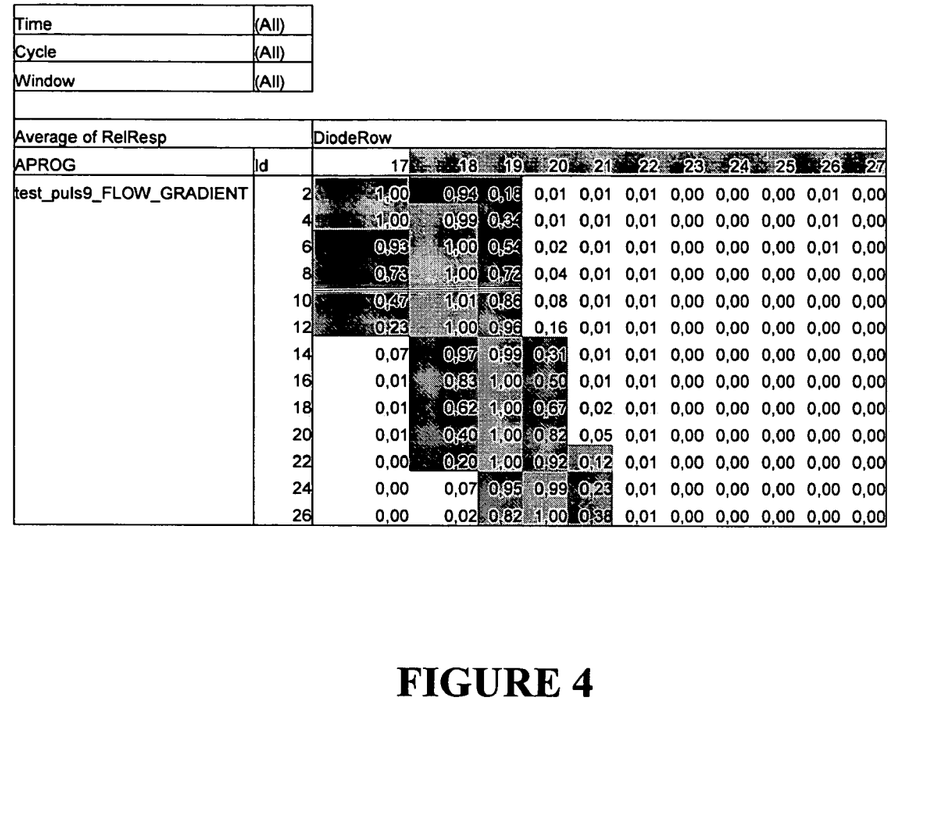
FIG. 4 is a pivot table showing relative detector responses across a flow cell surface with a laminar sample flow guided between two laminar flows of buffer.

The position of a sample fluid flow on a surface may be presented in various ways. An example is shown in FIG. 4 which is a pivot table (Microsoft® Excel) indicating the relative responses obtained at different detector rows as the sample flow is guided laterally across the sensing surface of a flow cell by two guiding buffers in a BIACORE® S51 system equipped with a ψ-cell (Biacore® S51 is a SPR-based biosensor instrument, normally equipped with two Y-type flow cells, each allowing a dual flow over the a sensor surface for hydrodynamic addressing; Biacore AB, Uppsala, Sweden). The total buffer flow was 100 μl/min, and the flow rates of the two buffer flows were changed in steps of 2 μl/min, starting with 2 μl/min for one buffer and 98 μl/min for the other. The sample fluid flow was 20 μl/min all the time. Relative responses >0.1 (i.e., 10% coverage of the detector row) are represented by dark areas in the table, while relative responses between 0.15 and 0.97 are represented by grey areas. This approach thus permits convenient visual monitoring of the sample fluid flow.

Figure 5:
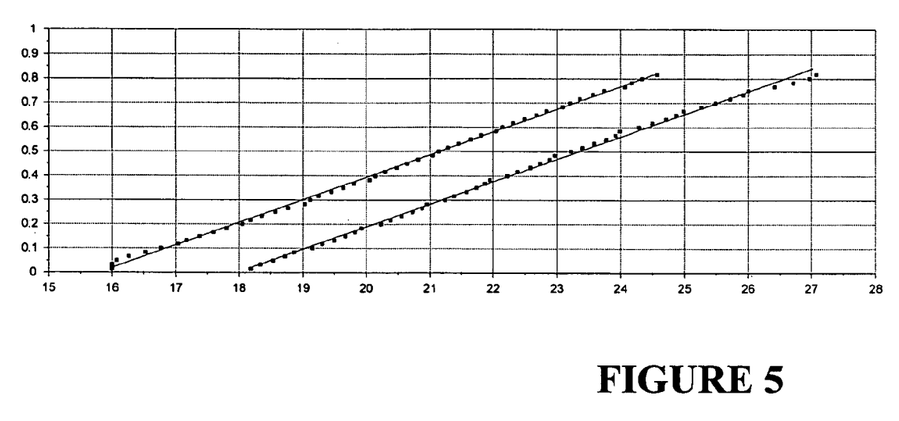
FIG. 5 is diagram showing the positions of the two interfaces between a sample flow and two guiding buffer flows on either side thereof.

Another way of presenting the position of the sample fluid flow, based on the same data as above, is shown in FIG. 5 which is a diagram indicating the positions of the two interfaces between sample flow and respective flows of guiding fluid for different settings of the guiding fluid flows. The vertical axis represents the fraction of the total buffer flow, and the horizontal axis represents the detector row numbers corresponding to the monitored flow cell areas. As seen from the Figure, both positioning and width of the sample flow may conveniently be read. Thus, by measuring in-situ and controlling the flows, both position and sample flow width may be controlled.

While positioning of the sample fluid flow via the interface between the two guiding fluid flows may be carried out manually, it is usually preferred that the positioning is at least semi-automated. An example of an algorithm for an automated positioning procedure which may be implemented by a computer program running software is schematically illustrated in the flow chart of FIG. 6.

Figure 6:
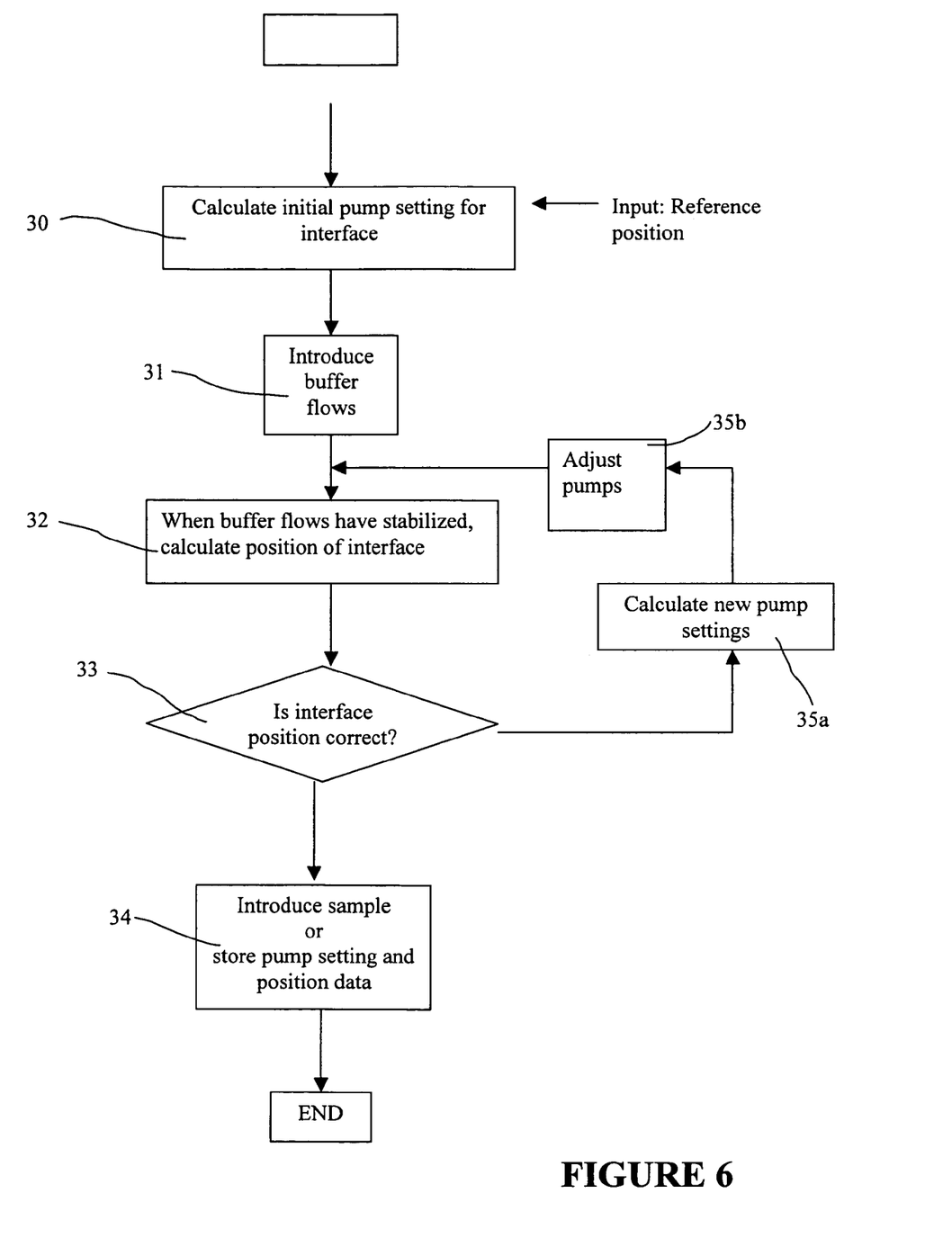
FIG. 6 is a flow chart showing a computer-implemented algorithm for sample flow positioning.

In the first step (30), a reference position for the interface is defined and an initial pump setting (the pumps for the guiding fluids) is calculated based on a basic calibration curve.

Then, the two guiding fluids are introduced by the pumps in the calculated initial setting (31).

After a sufficient time for the interface between the guiding fluids to stabilize, the position thereof is detected and calculated (32).

The interface position obtained is then compared with the reference position (33).

If the position is correct, sample fluid is introduced (34), or, in case of calibration, the pump setting and the position data are stored.

If the position is incorrect, new pump settings are calculated (35a) and the pumps are adjusted (35b). Steps 32, 33 and 35 are then repeated until the correct position is obtained.

With the interface correctly positioned, sample fluid is introduced, and the sample flow rate is increased until the desired sample flow width has been obtained. As described above, this may be performed by monitoring the position of at least one of the sample/guiding fluid interfaces.

The control of the width of the sample flow may, of course, also be semi-automated or automated, e.g., by a corresponding algorithm as that outlined above.

The invention therefore also extends to computer programs, particularly computer programs on or in a carrier, adapted for putting the sample flow positioning procedure of the invention into practice. The carrier may be any entity or device capable of carrying the program. For example, the carrier may comprise a storage medium, such as a ROM, a CD ROM or a semiconductor ROM, or a magnetic recording medium, for example a floppy disc or a hard disk. The carrier may also be a transmissible carrier, such as an electrical or optical signal which may be conveyed via electrical or optical cable or by radio or other means. Alternatively, the carrier may be an integrated circuit in which the program is embedded.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

It is to be understood that the invention is not limited to the particular embodiments of the invention described above, but the scope of the invention will be established by the appended claims.

The invention claimed is:

1. A method of positioning a laminar flow of a sample fluid on a surface within a flow cell, which method comprises the steps of:
    a) providing a laminar flow of a first guiding fluid adjacent to a laminar flow of a second guiding fluid different from the first guiding fluid such that the two fluids flow together over the surface with a detectable interface to each other,
    b) detecting the interface between the two different guiding fluids,
    c) optionally adjusting the interface laterally to a desired position by adjusting the relative flow rates of the two guiding fluids, and
    d) introducing a laminar flow of the sample fluid between the laminar flows of the first and second guiding fluids such that the flow of the sample fluid is sandwiched between the guiding fluids.

2. The method according to claim 1, wherein the width of the flow of sample fluid is controlled by detecting the positions of the interfaces to the respective guiding fluids, and displacing the interfaces laterally by adjusting the relative flow rate of the sample fluid.

3. The method according to claim 1, wherein the total flow rate through the flow cell is kept constant when the flow of the sample fluid is introduced.

4. The method according to claim 1, wherein the two guiding fluids have different refractive indices, and the position of the interface is detected by a shift in refractive index.

5. The method according to claim 4, wherein the position of the interface is detected by evanescent wave-based sensing.

6. The method according to claim 5, wherein the evanescent wave-based sensing is SPR-based sensing.

7. The method according to claim 1, wherein the flow cell is of ψ-type.

8. The method according to claim 1, wherein after step c) in claim 1, flow-related settings corresponding to the position of the interface are stored, and steps b) to c) are optionally repeated at least once to obtain calibrated flow-related settings for at least two different defined positions of the interface, and wherein before carrying out step d) in claim 1, calibrated settings for the first and second guiding fluids are applied to obtain laminar flows thereof with the interface at a desired defined position.

9. The method according to claim 8, wherein step d) is repeated at least once with the interface at a different defined position.

10. The method according to claim 1, which is computer-implemented.

11. A analytical system, comprising:
a sensor device comprising at least one flow cell, each flow cell having an inlet end and an outlet end, at least one sensing surface on a wall surface within the flow cell located between the inlet and outlet ends, wherein the flow cell has at least three inlet openings at the inlet end, and at least one outlet opening at the outlet end, such that separate laminar fluid flows entering the flow cell through the respective inlet openings can flow side by side through the flow cell over the sensing surfaces; and detection means capable of detecting changes at the sensing surface or surfaces; and
data processing means for performing the method as defined in claim 1.

12. A computer program comprising program code means for performing the method as defined in claim 1 when the program is run on a computer.

13. A computer program product comprising program code means stored on a computer readable medium or carried on an electrical or optical signal for performing the method as defined in claim 1 when the program is run on a computer.

14. A computer system containing a program for performing the method as defined in claim 1 when the program is run on a computer.

15. A method of positioning a laminar flow of a sample fluid on a surface within a flow cell, which method comprises:
A. performing a calibration procedure which comprises the steps of:
a) providing a laminar flow of a first guiding fluid adjacent to a laminar flow of a second guiding fluid different from the first guiding fluid such that the two fluids flow together over the surface with a detectable interface to each other,
b) detecting the interface between the two different guiding fluids,
c) optionally, adjusting the interface laterally to a defined position by adjusting the relative flow rates of the two guiding fluids,
d) storing flow rate-related settings corresponding to the position of the interface, and
B. performing a sample introduction procedure which comprises the steps of:
e) applying calibrated flow rate-related settings to the two guiding fluids to obtain laminar flows thereof with the interface at a defined position, and
f) introducing a laminar flow of the sample fluid between the laminar flows of the two guiding fluids such that the flow of the sample fluid is sandwiched between the two guiding fluids.

16. The method according to claim 15, wherein the guiding fluids when performing the sample introduction procedure are the first and second guiding fluids used when performing the calibration procedure.

17. The method according to claim 15, wherein the flow rate-related settings are settings for respective pump means for the guiding fluids.

18. The method according to claim 15, which is computer-implemented.

19. A analytical system, comprising:
a sensor device comprising at least one flow cell, each flow cell having an inlet end and an outlet end, at least one sensing surface on a wall surface within the flow cell located between the inlet and outlet ends, wherein the flow cell has at least three inlet openings at the inlet end, and at least one outlet opening at the outlet end, such that separate laminar fluid flows entering the flow cell through the respective inlet openings can flow side by side through the flow cell over the sensing surfaces; and detection means capable of detecting changes at the sensing surface or surfaces; and
data processing means for performing the method as defined in claim 15.

20. A computer program comprising program code means for performing the method as defined in claim 15 when the program is run on a computer.

21. A computer program product comprising program code means stored on a computer readable medium or carried on an electrical or optical signal for performing the method as defined in claim 15 when the program is run on a computer.

22. A computer system containing a program for performing the method as defined in claim 15, when the program is run on a computer.

23. The method of claim 15, further comprising the step of repeating steps c) and d) to obtain flow rate related settings for at least two different defined positions of the interface.

24. The method of claim 15, further comprising the step of repeating steps e) and f) at least once with the interface at a different defined position.

* * * * *